United States Patent [19]
Miltenberger et al.

[11] Patent Number: 5,637,761
[45] Date of Patent: Jun. 10, 1997

[54] PROCESS FOR THE CONTINUOUS PREPARATION OF ESTERS OF LOWER ALIPHATIC CARBOXYLIC ACIDS WITH LOWER ALCOHOLS

[75] Inventors: Karlheinz Miltenberger, Gersthofen; Manfred Schmidt, Günzburg-Deffingen; Karl Petz, Neusäss, all of Germany

[73] Assignee: Hoechst Aktiengesellschaft, Germany

[21] Appl. No.: 983,284

[22] Filed: Nov. 30, 1992

Related U.S. Application Data

[63] Continuation of Ser. No. 602,002, Oct. 23, 1990, abandoned.

[30] Foreign Application Priority Data

Oct. 25, 1989 [DE] Germany .......................... 39 35 470.9

[51] Int. Cl.$^6$ ................................................. C07C 69/63
[52] U.S. Cl. ........................................................ 560/226
[58] Field of Search ............................................. 560/226

[56] References Cited

U.S. PATENT DOCUMENTS

| | | | |
|---|---|---|---|
| 4,239,492 | 12/1980 | Andoh et al. | 560/205 |
| 4,329,492 | 5/1982 | Andoh et al. | 560/205 |
| 4,837,357 | 6/1989 | Merger et al. | 560/226 |

FOREIGN PATENT DOCUMENTS 0315096  5/1989  European Pat. Off. .

*Primary Examiner*—C. Warren Ivy
*Assistant Examiner*—S. Padmanabhan
*Attorney, Agent, or Firm*—Connolly & Hutz

[57] ABSTRACT

In the esterification of aliphatic $C_2$–$C_6$-carboxylic acids with aliphatic $C_1$–$C_4$-alcohols, the ester formed is removed by azeotropic distillation together with the water of reaction. After the water of reaction has been separated in a separating condenser, the ester phase is freed, by washing with water, from acid carried over, and water and alcohol are then removed by distilling off a small fraction of the ester.

In this way no salt-containing effluents are produced. The ester is obtained in a very good yield, free from acid and alcohol.

7 Claims, 1 Drawing Sheet

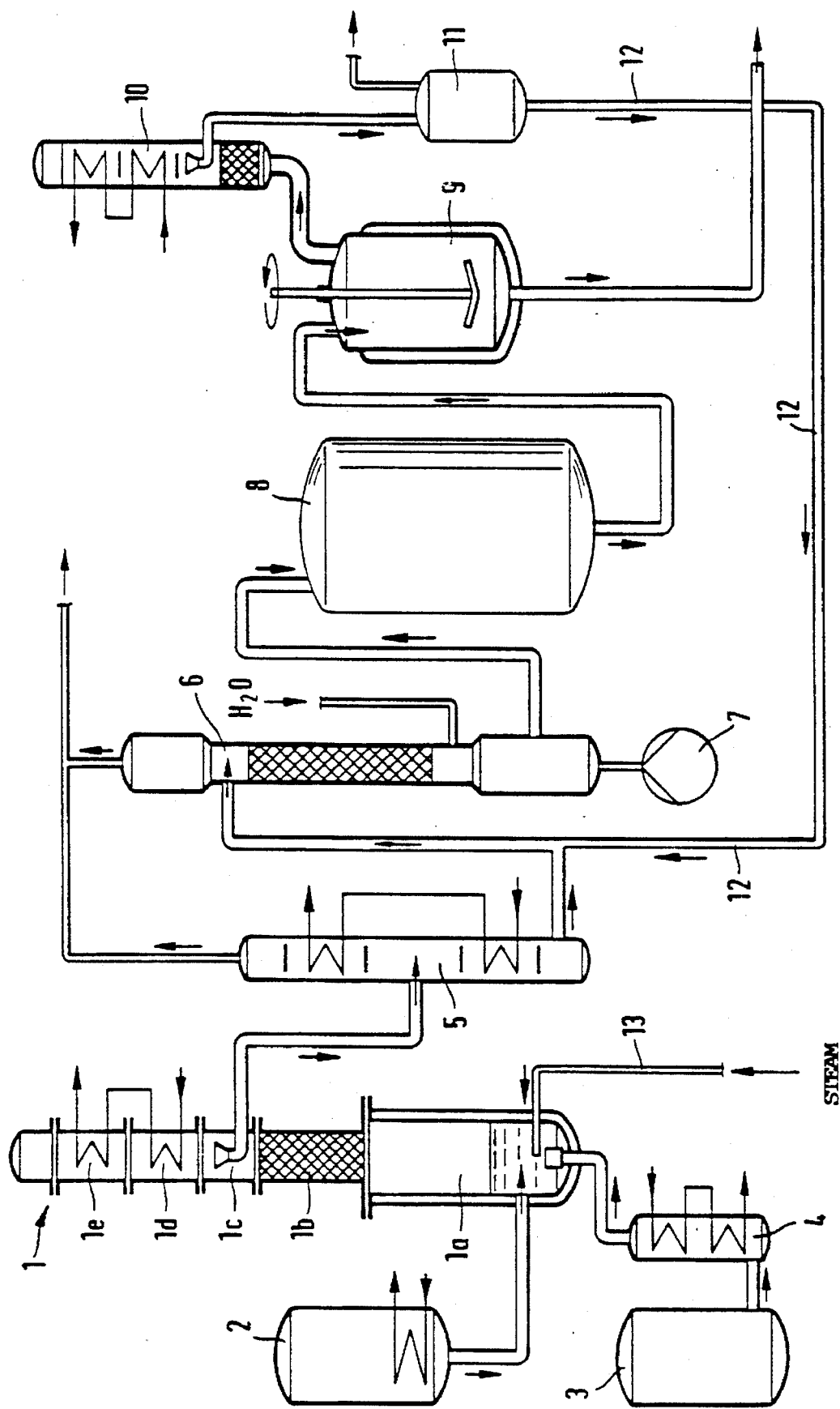

PROCESS FOR THE CONTINUOUS PREPARATION OF ESTERS OF LOWER ALIPHATIC CARBOXYLIC ACIDS WITH LOWER ALCOHOLS

This is a continuation of Ser. No. 07/602,002, filed Oct. 23, 1990, now abandoned.

The invention relates to a continuous process for the preparation of esters of lower aliphatic carboxylic acids with lower alcohols, in particular esters of monochloroacetic acid with $C_1$–$C_4$-alcohols.

A process is known for the preparation of esters of monochloroacetic acid with $C_1$–$C_4$-alcohols by esterifying the free acid with the alcohols in the presence of esterification catalysts, in which the alcohol is added to the melt of monochloroacetic acid, containing catalyst, with removal of the water of reaction, at such a rate that the water of reaction formed is removed by distillation as a virtually alcohol-free binary azeotrope, together with portions of the chloroacetic acid ester formed (cf. EP 315,096). The bulk of the ester is obtained as a bottom product and must be washed with aqueous bicarbonate solution in order to remove unreacted acid and the catalyst. Effluent containing salts is thereby produced.

The object was to find a continuous esterification process in which no salt-containing effluents are produced.

It has been found that the object can be achieved if the resulting ester is distilled off continuously and washed with water.

The invention therefore relates to a process for the preparation of an ester of a lower aliphatic $C_2$–$C_6$-carboxylic acid with a lower aliphatic $C_1$–$C_4$-alcohol by reacting the carboxylic acid with the alcohol at an elevated temperature in the presence of a catalyst with removal of the water of reaction by distillation, which comprises removing the ester formed together with the water of reaction by azeotropic distillation, washing the ester countercurrent with water after separating off the water of reaction and then freeing the ester from water and alcohol by distilling off a small fraction of the ester.

BRIEF DESCRIPTION OF THE DRAWING

The reactor (1) comprises a jacket heated lower section (1a), a length of packed column (1b), a reflux divider (1c) and a number of lengths of condenser (1d) and (1e). The reagents are fed into reactor (1) from a stock vessel (3) via a heat exchanger (4) or from a heated stock vessel (2). A condensate is obtained in a separating condenser (5) and washed countercurrent with water in a wash column (6) in order to remove an excess of acid, the contents of the column being put into a pulsating motion by means of a pulsating pump (7) in order to increase the washing effect. Via the intermediate vessel (8) the washed product is fed into a distillation boiler (9) equipped with a small column (10) and a receiver (11). The distillate returns to the wash column via line (12).

The process according to the invention is carried out in the following way.

The acid to be esterified is initially placed, in liquid form, in a reaction vessel and the alcohol is introduced, preferably in the form of vapor, into the acid at the base of the reaction vessel. If vapor is introduced it is appropriate to use a nozzle; if the liquid alcohol is introduced a simple tube is adequate. In the course of this a forced circulation of the mixture is achieved by means of the vaporizing alcohol. The catalyst is present in the acid initially taken. The reaction products, ester and water, are distilled off; their vapors are passed through a short rectification column equipped with a reflux divider. By selecting a suitable reflux ratio, which depends on the nature of the ester and on the reaction temperature, the amount of acid and alcohol carried over can be reduced to a minimum. The following relationship has been found for esters of monochloroacetic acid

| Ester | Reaction temperature | |
|---|---|---|
| MME | approx. 125° C. | ⎫ |
| MEE | approx. 135° C. | ⎬ 9:1 to 4:1 |
| MIPE | approx. 139–140° C. | ⎭ |

MME = methyl ester,
MEE = ethyl ester,
MIPE = isopropyl ester

If the reaction temperature is increased, the content of monochloroacetic acid in the ester rises and the alcohol content falls. If the temperature is reduced, the alcohol content rises and the acid content falls. Acid and alcohol are replenished at the same rate as the resulting ester is distilled off together with the water of reaction. The mixture then passes into a separating condenser, where a spontaneous separation into an aqueous phase and an ester phase takes place. The water phase is passed to the preparation stage, where the residual amounts of ester, acid and alcohol are removed from it. The ester phase is transferred from the separating condenser to a wash column and is there washed counter-current with water. It is preferable for the column to be equipped with a pulsation pump in order to intensify the washing effect. The ester, which is now free from acid, is freed from residues of water and alcohol. A falling film evaporator operated under a slight vacuum is suitable for this purpose. Batchwise working is also possible, however. This is effected by passing the ester batchwise via a buffer vessel into a distillation boiler, where water, alcohol and a small proportion (not more than 10%) of ester are distilled off (removed by topping) under a slight vacuum. The ester leaving the distillation boiler is free from byproducts. The distillate is separated, the ester phase being recycled to the wash column and the water phase being passed to the preparation stage. Acid and alcohol recovered in the preparation stage are re-introduced into the esterification stage. The residual water can be discharged to the drain.

Lower aliphatic carboxylic acids having 2 to 6 carbon atoms are esterified by the process according to the invention. It is preferable to employ the lower halogenocarboxylic acids, such as, for example, chloroacetic acids or chloropropionic acids, in particular monochloroacetic acid.

The alcohols to be used are aliphatic $C_1$–$C_4$-alcohols, for example methanol, ethanol and isopropanol.

The acid and alcohol are so selected that the ester formed is still liquid at temperatures around 20° C. and preferably has a density greater than water.

The catalyst used is a known esterification catalyst, such as, for example, $AlCl_3$, concentrated sulfuric acid, methanesulfonic acid, ethanesulfonic acid, p-toluenesulfonic acid or a similar acid, preferably sulfuric acid or methanesulfonic acid. The amount employed is 0.1 to 1% of the amount of acid present in the reaction vessel.

The reaction temperature is 100° to 150° C., preferably 125° to 140° C.

The process according to the invention affords a pure ester in a high yield. Effluents containing salt are not as a rule produced.

The following examples are intended to illustrate the invention.

EXAMPLE 1

Methyl monochloroacetate (MME) was prepared in an apparatus as shown in the diagram.

The reactor used (1) comprised a Jacket-heated enameled lower section (1a), a length of column packed with Raschig rings (1b) a reflux divider (1c) and two lengths of condenser (1d) and (1e) made of glass. The lower section of the reactor contained approx. 650 kg of melted monochloroacetic acid (=approx. 70% of its volume) and 5 liters of concentrated sulfuric acid, at a temperature of 125° C. 155 kg per hour of methanol in the form of vapor were introduced into the reactor at a temperature of 108° C. from the stock vessel (3) via the heat exchanger (4). As a result of the removal by distillation of methyl ester and water, 400 kg/hour of monochloroacetic acid flowed from the heated stock vessel (2) into the reactor. The reflux ratio in the column (1b)–(1e) was controlled via a timing regulator and was set to 1:7.5 (take-off). An equilibrium between the reactants was thus formed in the reactor.

After distillation had started, a condensate which spontaneously separated into two phases was obtained in the separating condenser (5). The heavier, lower phase was the ester phase, totalling 489 kg/hour. It had the following composition:

| MME | 91.3% |
|---|---|
| Methanol | 2.9% |
| MA | 1.3% |
| Water | 4.5% |

(MA = monochloroacetic acid)

66 kg/hour of water of reaction were obtained as the upper phase:

| Water | 83,7% |
|---|---|
| Methanol | 10.0% |
| MA | 1.3% |
| MME | 5.0% |

This water of reaction was passed to the preparation stage. The crude ester was washed countercurrent with 795 dm³/hour of water in the wash column (6) in order to remove the monochloroacetic acid, the contents of the column being put into a pulsating motion by means of a pulsation pump (7) in order to increase the washing effect.

The products leaving the washing column (6) were 423 kg/hour of ester having the composition:

| MME | 98.2% |
|---|---|
| Methanol | 0.2% |
| Water | 1.6% | and 860 kg/hour of wash water having the composition:

| Water | 94.5% |
|---|---|
| MME | 3.3% |
| Methanol | 1.5% |
| MA | 0.7%. |

The ester was first transferred to the intermediate vessel (8). Portions of 4500 kg of ester were fed as required from this intermediate vessel (8) into the distillation boiler (9), and about 10% of the ester was distilled off in the course of approx. 4 hours at 80 to 85° C. and 0.15 to 0.20 bar. The ester remaining in the boiler (9) was free from acid and methanol. The portion of ester distilled off via the small column (10) and separated in the receiver (11) contained:

| MME | 81% |
|---|---|
| Methanol | 1.6% |
| Water | 17.5% | and was fed to the wash column via the line (12).

The yield was approx. 100 kg/hour of pure methyl monochloroacetate, i.e. 97 to 98%, relative to the acid employed, and 88 to 89% relative to the methanol employed.

EXAMPLE 2

Ethyl monochloroacetate (MEE) was prepared in the same apparatus as in Example 1, with the following data:

| Reaction temperature | 135° C. |
|---|---|
| Monochloroacetic acid | 315 kg/hour |
| Ethanol | 186 kg/hour |
| Catalyst | $H_2SO_4$, approx. 1% |
| Reflux ratio | 1:5 |
| Crude ester from the separating condenser (5) 436 kg/hour | |

| MEE | 90.1% |
|---|---|
| Ethanol | 5.1% |
| MA | 1.9% |
| Water | 2.9% |
| Water of reaction 65 kg/hour | |

| Water | 91.4% |
|---|---|
| Ethanol | 5.3% |
| MA | 2.0% |
| MEE | 1.3% |
| Ester from wash column (6) 377 kg/hour | |

| MEE | 98.3% |
|---|---|
| Ethanol | 0.6% |
| Water | 1.1% |
| Wash water from wash column (6) 818 kg/hour | |

| Water | 94.4% |
|---|---|
| Ethanol | 2.4% |
| MA | 1.0% |
| MEE | 2.2% |

The ester was topped batchwise as required at 90° to 95° C. and 0.15 to 0.20 bar. Yield of acid-free and ethanol-free ester 96 to 97%, relative to acid employed, and 81 to 82% relative to ethanol employed. Water content not more than 0.01%.

EXAMPLE 3

Isopropyl monochloroacetate was prepared in the same apparatus as in Example 1.

| | |
|---|---|
| Reaction temperature | 135–140° C. |
| Monochloroacetic acid | 62 kg/hour |
| Isopropanol | 55 kg/hour |
| Catalyst | sulfuric acid, 0.1% |
| Steam through line (13), to reduce side-reactions, 3 bar | |
| | 20 kg/hour |
| Reflux ratio | 1:5 (take-off) |
| Crude ester from separating condenser (5) 100 kg/hour | |
| MIPE | 83.0% |
| Isopropanol | 7.2% |
| MA | 1.8% |
| Water | 8.0% |
| Water of reaction from separating condenser (5) | |
| 33 kg/hour | |
| Water | 93.5% |
| Isopropanol | 3.6% |
| MA | 2.4% |
| MIPE | 0.5% |
| Ester from wash column (6) 92 kg/hour | |
| MIPE | 98.9% |
| Isopropanol | 0.2% |
| Water | 0.9% |
| Wash water from wash column 215 kg/hour | |
| Water | 95.1% |
| Isopropanol | 3.2% |
| MA | 0.8% |
| MIPE | 0.9% |

The ester obtained after drying was free from acid and isopropanol:

| | |
|---|---|
| MIPE | 99.7% |
| Diisopropyl ether | 0.2% |
| Water | 0.1% |

Yield 90 to 91%, relative to acid employed, and 72 to 75%, relative to isopropanol employed.

In the esterification of monochloroacetic acid with isopropanol the proportion of monochloroacetic acid carried over has increased markedly because of the higher esterification temperature. In addition, side-reactions, such as the formation of diisopropyl ether and propene by the elimination of water from isopropanol, make themselves evident. These side-reactions can be repressed by the introduction of steam.

EXAMPLE 4

Approx. 1200 g/hour of a mixture of 9044 g of 96% 1-chloropropionic acid (=80 mol) and 2715 g of methanol (=85 mol) were esterified at a temperature of 100 to 105° C. in a laboratory apparatus comprising a 500 cm$^3$ four-necked flask equipped with a stirrer, an inlet tube for acid/methanol mixture, a ground-joint thermometer and an upright silvered vacuum column of length 1 m and diameter 3 cm, a high-efficiency condenser and a receiver. For this purpose the whole of the 1-chloropropionic acid was dissolved in methanol outside the apparatus. Approx. 250 cm$^3$ of the 1-chloropropionic acid/methanol solution was initially placed, without catalyst, in the 500 cm$^3$ four-necked flask. The oil bath was heated up, and an ester/water mixture was distilled off through the column at 100°–105° C. and a reflux ratio of 1:5 (take-off). The rest of the reaction mixture was metered in continuously into the base of the flask via the inlet tube. Metering was carried out at the same rate as the removal by distillation of the ester/water mixture (approx. 1 liter/hour). The crude ester and the water of reaction were collected separately and had the following composition:

| CG analysis | Crude CPE | Water of reaction |
|---|---|---|
| ? | 0.02% | 0.02% |
| Methanol | 3.33% | 8.90% |
| ? | 0.08% | — |
| Water | 0.90% | 89.24% |
| CPE | 92.10% | trace |
| ? | 0.12% | — |
| DCPE | 3.05% | — |
| 1-chloropropionic acid | 0.40% | 1.90% |

The yield of crude ester was approx. 92%.

The crude ester was then washed countercurrent with a four-fold amount of water, at a rate of 0.35 kg/hour, in a glass column of length 1 m and diameter 30 mm, packed with Raschig rings (φ 6 mm). Since the mixing of the reactants was evidently not optimal, the content of 1-chloropropionic acid was only reduced from 0.40% to 0.14. Because of this, washing with a bicarbonate solution was carried out subsequently. The ester then had the following composition:

| | |
|---|---|
| ? | 0.22% |
| Methanol | 1.93% |
| Water | 0.50% |
| CPE | 93.78% |
| DCPE | 3.55% |
| ? | 0.08% |

600 g portions of this ester were subjected to column distillation in a 1 dm$^3$ round-bottomed flask at 60° C. and a pressure of 0.13 bar. When 4 to 5% had been distilled off, the ester had the composition:

| | |
|---|---|
| Methanol | 0.11% |
| Water | 0.04% |
| CPE | 95.90% |
| DCPE | 3.90% | and was adequately pure for further processing.

We claim:

1. A continuous process for the preparation of an ester of a lower aliphatic $C_2$–$C_6$-carboxylic acid wherein said carboxylic acid is chloroacetic acid or chloropropionic acid, with a lower aliphatic $C_1$–$C_4$-alcohol by reacting the carboxylic acid with the alcohol at an elevated temperature wherein said elevated temperature ranges in value from 100° C. to 150° C., in the presence of a catalyst wherein said catalyst is sulfuric acid or methanesulfonic acid, with removal of the water of reaction of distillation, which comprises removing the ester formed together with the water of reaction by azeotropic distillation, while replenishing the acid and alcohol at the same rate as ester and water of reaction is removed washing the ester countercurrent with water after separating off the water of reaction and then freeing the ester from water of and alcohol by distilling off a small fraction of the ester.

2. A process as claimed in claim 1, wherein monochloroacetic acid is esterified.

3. The process of claim 1, wherein said temperature ranges in value from 125° C. to 140° C.

4. The process as claimed in claim 1, wherein said aliphatic $C_1$–$C_4$ alcohol is methanol, ethanol, or isopropanol.

5. The process as claimed in claim 1, wherein said ester formed is a liquid at a temperature of around 20° C.

6. The process as claimed in claim 5, wherein said ester has a density greater than water.

7. The process as claimed in claim 1, wherein more than 98% of the ester distilled.

* * * * *